(12) United States Patent
Jun et al.

(10) Patent No.: US 8,047,074 B2
(45) Date of Patent: Nov. 1, 2011

(54) HUMIDITY SENSOR AND METHOD OF MANUFACTURING THE SAME

(75) Inventors: Chi Hoon Jun, Daejeon (KR); Sang Choon Ko, Daejeon (KR); Chang Auck Choi, Daejeon (KR); Byoung Gon Yu, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 77 days.

(21) Appl. No.: 12/617,701

(22) Filed: Nov. 12, 2009

(65) Prior Publication Data

US 2010/0147070 A1 Jun. 17, 2010

(30) Foreign Application Priority Data

Dec. 17, 2008 (KR) .................. 10-2008-0128848

(51) Int. Cl.
*G01N 27/12* (2006.01)
(52) U.S. Cl. ...................... 73/335.05; 73/31.06
(58) Field of Classification Search .............. 438/49, 438/50, 52, 53; 73/31.06, 335.05
See application file for complete search history.

(56) References Cited

U.S. PATENT DOCUMENTS

| | | | |
|---|---|---|---|
| 5,019,885 A * | 5/1991 | Yagawara et al. ............... 73/23.4 |
| 5,563,341 A * | 10/1996 | Fenner et al. ............... 73/335.11 |
| 6,690,569 B1 | 2/2004 | Mayer et al. |
| 6,906,392 B2 * | 6/2005 | Benzel et al. .................. 257/414 |
| 7,373,819 B2 | 5/2008 | Engler et al. |
| 2005/0199041 A1* | 9/2005 | Weber et al. .................. 73/31.06 |
| 2006/0237551 A1 | 10/2006 | Engler et al. |
| 2007/0062812 A1* | 3/2007 | Weber et al. ................... 204/431 |
| 2008/0134753 A1* | 6/2008 | Jun et al. ......................... 73/23.2 |
| 2009/0151429 A1* | 6/2009 | Jun et al. ....................... 73/31.06 |

FOREIGN PATENT DOCUMENTS

JP 2006-153512 6/2006
KR 1020050076524 A 7/2005

* cited by examiner

*Primary Examiner* — Lisa Caputo
*Assistant Examiner* — Punam Roy

(57) ABSTRACT

Provided are a humidity sensor and a method of manufacturing the same. The humidity sensor has high sensitivity, quick response time, improved temperature characteristics, low hysteresis and excellent durability. Moreover, for the humidity sensor, a humidity sensitive layer may be formed of various materials. The humidity sensor may be manufactured in a small size on a large scale.

The humidity sensor includes a substrate, an open cavity with an open upper portion formed to have a depth and a width in the substrate, a plurality of electrode pads formed on the substrate, a heater connected to one pad of the electrode pads at one end, and connected to another pad of the electrode pads at the other end to be suspended over the open cavity, a plurality of sensing electrodes formed on the same plane as the heater, and suspended over the open cavity to output a sensed signal to the electrode pads, a humidity sensitive layer formed on the heater and the sensing electrodes, suspended over the open cavity, and changed in characteristic according to the humidity, and an ambient temperature measurement part configured to measure the temperature around the humidity sensor, wherein the temperature is used as a reference temperature to control a heating temperature of the heater.

18 Claims, 8 Drawing Sheets

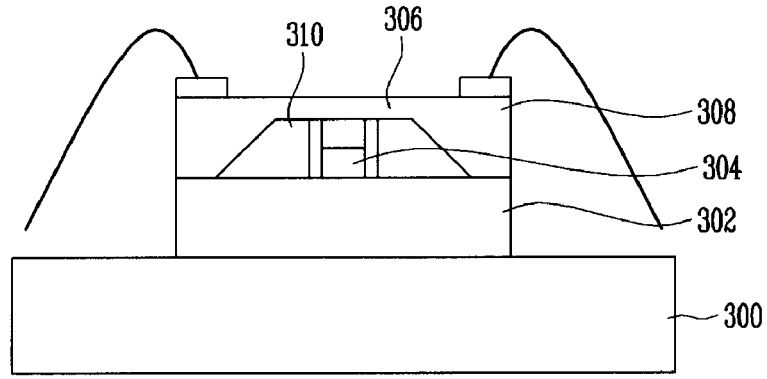
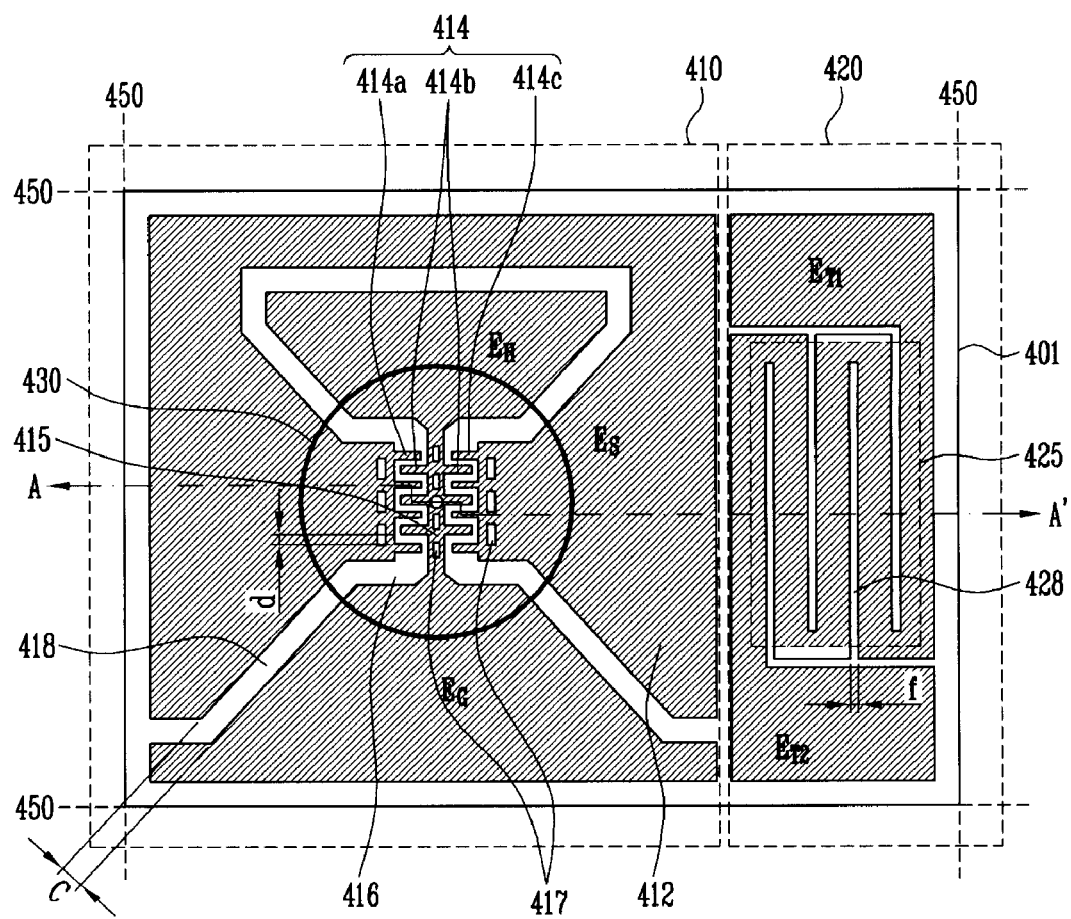

HUMIDITY SENSOR AND METHOD OF MANUFACTURING THE SAME

CROSS-REFERENCE TO RELATED APPLICATION

This application claims priority to and the benefit of Korean Patent Application No. 10-2008-0128848, filed Dec. 17, 2008, the disclosure of which is incorporated herein by reference in its entirety.

BACKGROUND

1. Field of the Invention

The present invention relates to a humidity sensor and a method of manufacturing the same, and more particularly, to a humidity sensor which has high sensitivity and quick response properties, consumes less power to heat, has fast heating and cooling properties and high durability and is manufactured in an ultra small size, and a method of manufacturing the humidity sensor. The humidity sensor may use various kinds of materials to form a humidity sensitive layer, and may be mass-produced at low production costs in a simple process.

2. Discussion of Related Art

Recently, with growing interest in a ubiquitous environment for obtaining information about things centered around humans, there is an increasing need to develop high-performance sensors capable of obtaining exact and various information in a short period of time.

Among them, a primary core sensor providing ubiquitous service may be a sensor capable of obtaining surrounding information including daily information such as weather conditions. Specifically, daily information such as humidity is the most useful primary information in real life, and a high-performance humidity sensor is needed to realize such ubiquitous service.

This humidity sensor may be used individually or together with sensors obtaining different kinds of information to be applied to logistics service, transport service and a transportation network, thereby improving related services. In addition, it may be applied to production and factory managements and construction of an environmental network in agriculture, fisheries, livestock industries, distribution industries and manufacturing industries, and also applied to home automation, office networks and building control in order to create comfortable housing space or to prevent other harmful industrial environments.

To apply the various services, studies on increasing sensitivity, reducing size and production costs and ensuring reliability for a humidity sensor are under way. In a structural aspect, a humidity sensor has recently evolved into an ultra small-sized micro sensor mainly utilizing microelectromechanical system (MEMS) technology due to the application of semiconductor processing technology from a conventional ceramic sintered or thick film structure.

However, today, the most widely used measurement method for the humidity sensor is a relatively simple method of measuring humidity by measuring electrical characteristics when moisture is adsorbed on or released from a sensitive layer generally formed of an organic material such as a polymer or an inorganic material such as ceramic. Usually, the humidity sensor using such a sensitive layer includes only a humidity sensitive layer and a sensing electrode, and quantifies humidity by detecting a property change of the sensitive layer according to the humidity.

However, the conventional humidity sensor using the sensitive layer has low sensitivity since it uses a planar electrode, and responds with high hysteresis in response to its surroundings. In addition, since the sensitive layer is difficult to reset to an initial state, its response time is several minutes. In the conventional humidity sensor, a large drift in performance is shown due to condensation of moisture on a sensor electrode or a sensitive layer, and durability is decreased due to high stress generated in the sensor structure when humidity is high.

In order to solve these problems, a novel structure has been recently designed, and efforts to facilitate reset of the sensitive layer to the initial state by appropriately heating the sensitive layer using a heater, minimize hysteresis and increase sensitivity are being made. The heater used for the humidity sensor directly affects the sensitivity, hysteresis, reset time, response time, main factors used to measure a performance drift and durability, so that exact and fast temperature control is required for the heater.

Meanwhile, micro humidity sensor devices studied so far have used at least 3 to 10 pattern masks to form functional elements including a thermal insulation structure, and have been manufactured by sequentially stacking the functional elements in a vertical direction on a substrate through a repeated process of thin film deposition, photoresist coating, micro patterning, and thin film etching. Accordingly, when the micro humidity sensor device is manufactured by a semiconductor process, it requires high production costs and a long manufacture period, leading to a decreasing yield. In order to effectively heat a humidity sensitive layer, a micro heater uniformly heating a local corresponding region is suitable, and most of all, this structure should consume low power. In addition, since the humidity sensor should be stably operated for several years, decrease of durability due to thermal stress applied to a sensor structure as the humidity sensor is repeatedly heated and cooled at predetermined temperature by a heater must be prevented.

Various materials for a humidity sensitive layer having an essential role in the humidity sensor have been studied, which include an organic material such as a polymer, a metal oxide, an inorganic material such as ceramic or semiconductor, and a nano material such as nano wires or nano tubes. Generally, a humidity sensitive layer is formed by directly micro-patterning a material for a sensitive layer on a surface of a sensor device using pattern masks, or by micro-aligning a sensor device and then dropping a source material. However, these methods have a problem in developing a unique forming process for a humidity sensitive layer material to be used. Thus, technology capable of easily forming a micro pattern at a specific position on the humidity sensor device is needed to use various materials as the humidity sensitive layer.

A conventional humidity sensor using micro processing technology and problems of the humidity sensor will be described below.

FIG. 1 is a cross-sectional view of a conventional humidity sensor.

The conventional humidity sensor of FIG. 1 is designed to increase the lifespan and reliability of the humidity sensor by reducing a change in characteristic of a sensing electrode according to the time. The conventional humidity sensor has a typical structure of a humidity sensor in which a cavity 102 is formed by anisotropically wet etching a back side of a silicon substrate 100 by its thickness through bulk micromachining, and a heater 110, a sensing electrode and a humidity sensitive layer are formed on a membrane 106 surrounded by insulating layers 104 and 108.

The conventional method using wet etching of silicon to manufacture the humidity sensor is relatively simple. However, it cannot control the depth and shape of the cavity 102, both sides of the substrate must be processed, and production costs are raised as the device's die becomes larger. Moreover, according to this method, a support layer is formed only of the insulating layer 104 in a suspended structure, so that it is vulnerable to repetitive thermal shock and also weak in structure.

FIG. 2 is a cross-sectional view of another conventional humidity sensor.

The conventional humidity sensor of FIG. 2 is designed in a structure capable of minimizing moisture condensation, and thus stably measuring humidity. The humidity sensor uses two substrates, in which a resistance heater 204 is formed on a lower substrate 200 by printing, a humidity sensitive element 206 is formed on an upper substrate 202 and then the upper substrate 202 is mounted on the lower substrate 200. During operation, the humidity sensitive element 206 on the upper substrate is heated to a predetermined temperature of a dew point or higher using the resistance heater 204 on the lower substrate 200 to prevent moisture condensation on the sensor.

Since the heater is formed by special patterning such as printing, and one substrate is mounted on the other substrate, so that they cannot be formed by a standard semiconductor process, the humidity sensor having such a structure is manufactured at high production costs, has low yield and is difficult to form in a small size. Moreover, due to the presence of the resistance heater 204 on a bulk substrate, thermal insulation cannot be sufficiently performed, and thus great amounts of heat are lost and power consumption is increased.

FIG. 3 is a cross-sectional view of still another conventional humidity sensor.

The conventional humidity sensor of FIG. 3 has a structure in which a cavity 310 and a membrane are formed by wet etching a back side of a silicon wafer 308 through bulk micromachining, a stress sensor 306 such as a piezoelectric material is formed thereon, a humidity sensitive layer pattern 304 is separately formed on a base 302 capable of alignment, and these two structures are aligned and assembled on another substrate 300 to allow the humidity sensitive layer pattern 304 to be in contact with the membrane in the cavity 310 formed in the silicon wafer 308. Accordingly, the humidity sensor using mechanical transformation in which a property change of the humidity sensitive layer pattern 304 according to the humidity turns into a stress change of the membrane is realized.

The method of manufacturing a humidity sensor described above cannot solve fundamental problems of humidity sensors, such as hysteresis, because a heater is not included in the humidity sensor formed in a microstructure. In addition, the humidity sensor is manufactured by wet etching, so that the depth and shape of the microstructure cannot be controlled, and the humidity sensor is manufactured by aligning and assembling several structures, so that the production costs are increased.

Meanwhile, most known methods of manufacturing a micro humidity sensor generally use a silicon substrate having very high thermal conductivity. Accordingly, in order to reduce thermal loss, an etched pit or groove is formed in a sensor structure by bulk micromachining to form a suspended structure separated from a substrate, and a heater, an insulting layer and a humidity sensitive layer are sequentially formed on this suspended structure, thereby somewhat reducing heat loss. However, since this process must be performed on both sides of a substrate, it requires high production costs, and since this is a wet etching process using crystal orientation of the substrate itself, the depth and shape of a thermal insulation structure cannot be freely controlled. Moreover, this method has a limitation in manufacturing a small-sized sensor device and has difficulty in compatibility with a standard CMOS semiconductor process, due to the usage of a special etchant such as potassium hydroxide (KOH).

Therefore, there is a need for a humidity sensor having improved characteristics and manufactured by a simple and economical process, and a method of manufacturing the same.

SUMMARY OF THE INVENTION

The present invention is directed to a humidity sensor having high sensitivity, quick response time and low hysteresis, and a method of manufacturing the same.

The present invention is also directed to a humidity sensor easily using various materials as a humidity sensitive layer, and a method of manufacturing the same.

The present invention is also directed to a humidity sensor having improved temperature characteristics, low power consumption and excellent durability, and a method of manufacturing the same.

The present invention is also directed to a humidity sensor easily produced at a low cost on a large scale, and a method of manufacturing the same.

One aspect of the present invention provides a humidity sensor, including: a substrate; an open cavity with an open upper portion, the open cavity being formed to have a depth and a width in the substrate; a plurality of electrode pads formed on the substrate; a heater connected to one pad of the electrode pads at one end and connected to another pad of the electrode pads at the other end to be suspended over the open cavity; a plurality of sensing electrodes formed on the same plane as the heater, and suspended over the open cavity to output a sensed signal to the electrode pad; a humidity sensitive layer formed on the heater and the sensing electrodes, suspended over the open cavity, and changed in characteristic according to the humidity; and an ambient temperature measurement part configured to measure the temperature around the humidity sensor, wherein the temperature is used as a reference temperature to control a heating temperature of the heater.

Another aspect of the present invention provides a method of manufacturing a humidity sensor, including: forming an insulating layer on a substrate; forming an electrode pad pattern, a heater pattern, a sensing electrode pattern, a resistance temperature detector (RTD) pattern and an electrode pad pattern for temperature measurement by patterning the insulating layer using a pattern mask; forming an open cavity in the substrate to suspend the heater pattern and the sensing electrode pattern; forming an electrode pad, a heater, sensing electrodes, an RTD and an electrode pad for temperature measurement by depositing a conductive layer on the electrode pad pattern, the heater pattern, the sensing electrode pattern, the RTD pattern and the electrode pad pattern for temperature measurement; and forming a humidity sensitive layer to cover the heater and the sensing electrodes.

BRIEF DESCRIPTION OF THE DRAWINGS

The above and other objects, features and advantages of the present invention will become more apparent to those of ordinary skill in the art by describing in detail preferred embodiments thereof with reference to the attached drawings in which:

FIGS. 1 to 3 are cross-sectional views of conventional humidity sensors;

FIGS. 4A and 4B are diagrams of a humidity sensor according to an exemplary embodiment of the present invention;

DETAILED DESCRIPTION OF EXEMPLARY EMBODIMENTS

Hereinafter, the present invention will be described with reference to the accompanying drawings in detail. This invention may, however, be embodied in different forms and should not be construed as limited to the embodiments set forth herein. Rather, these embodiments are provided so that this disclosure will be thorough and complete, and will fully convey the scope of the invention to those skilled in the art. Like numbers refer to like elements throughout the specification.

Throughout the specification, one part "includes" a component, which, not illustrated otherwise, does not mean another component is omitted, but another component may be further included.

Figure 4B:
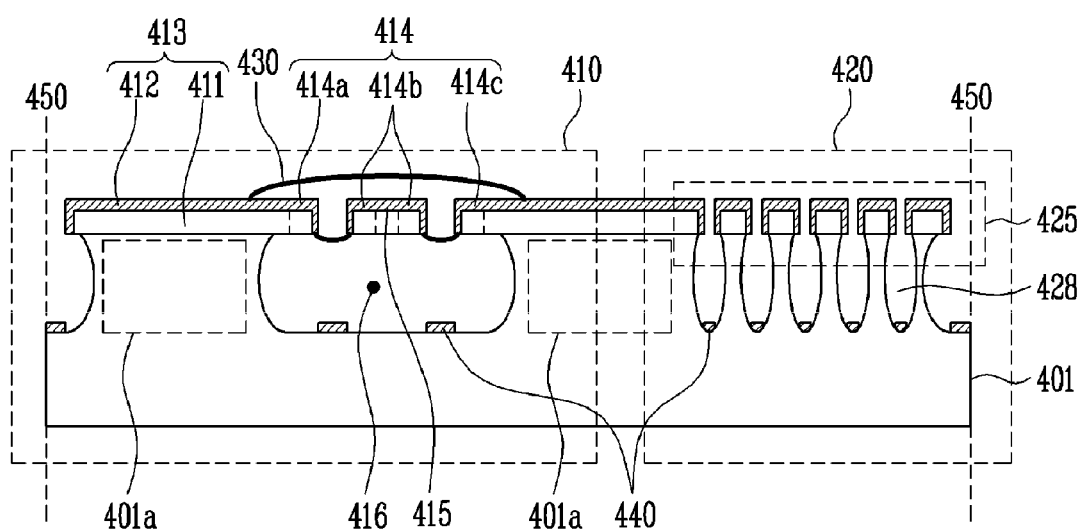

FIG. 4A is a plan view of a humidity sensor according to an exemplary embodiment of the present invention, and FIG. 4B is a cross-sectional view taken along line A-A' of FIG. 4A.

Referring to FIGS. 4A and 4B, the humidity sensor according to an exemplary embodiment of the present invention includes a substrate 401, a humidity measurement part 410 formed in one region of the substrate 401, and an ambient temperature measurement part 420 formed in another region of the substrate 401.

The substrate 401 provides regions for the humidity and temperature measurement parts 410 and 420, and may be formed of a semiconductor, a conductor or an insulator.

The humidity measurement part 410 is configured to measure ambient humidity, and includes an open cavity 416 formed to have depth and width in a predetermined region of the substrate 401, an anchor 401a configured to support structures to be formed on the substrate 401, a plurality of electrode pads $E_H$, $E_S$ and $E_G$ configured to communicate signals with outside, a plurality of sensing electrodes 414 configured to sense a change in humidity, a heater 415 configured to heat a humidity sensitive layer 430, and the humidity sensitive layer 430 formed on the sensing electrodes 414 and the heater 415.

When the humidity sensitive layer 430 is heated by the heater 415, the open cavity 416 serves to minimize thermal loss to the substrate 401. An upper portion of the open cavity 416 is open, and the open cavity 416 is formed in the substrate 401 to have depth and width. As the width or depth of the open cavity 416 is increased, the thermal loss to the substrate 401 is decreased. Thus, the open cavity 416 may be formed to a depth of about 1 to 500 μm and a width of about 1 μm to 10 mm.

When the open cavity 416 is formed under the heater 415, the sensing electrodes 414 and the humidity sensitive layer 430, these structures are suspended in the air, thereby minimizing the thermal loss to the substrate 401. As a result, the humidity sensitive layer 430 may be effectively heated with a small amount of power.

Due to the humidity sensitive layer 430 suspended by the open cavity 416, thermal mass is reduced, and thus the humidity sensitive layer 430 may be more rapidly heated or cooled.

The anchor 401a extends in a vertical direction from the substrate 401 and supports the structures formed on the substrate 401.

Five electrode pads $E_H$, $E_S$ and $E_G$, $E_{T1}$ and $E_{T2}$ are formed by sequentially stacking an insulating layer 411 and a conductive layer 412 on the substrate 401, and serve to communicate signals with an external circuit (not shown). Each electrode pad $E_H$, $E_S$, $E_G$, $E_{T1}$ or $E_{T2}$ has a predetermined depth and width, is insulated from other electrode pads by an electrode pad separation groove 418 and a resistance temperature detector (RTD) separation groove 428, which are formed on the substrate 401, and is also insulated from the substrate 401.

The heater 415 is formed by sequentially stacking the insulating layer 411 and the conductive layer 412, and formed on the same plane as the electrode pads $E_H$, $E_S$, $E_G$, $E_{T1}$ and $E_{T2}$. In addition, the heater 415 is suspended on the open cavity 416 and extends from one electrode pad $E_H$ to another electrode pad $E_G$, resulting in formation of a bridge structure. The heater 415 may be designed to have a resistance of several to several hundreds of ohms at room temperature.

The heater 415 may include microelectrode fingers attached at both sides in a cantilever array, resulting in a comb or fishbone shape. Here, the microelectrode fingers formed at both sides of the heater 415 serve as heat spreaders which laterally spread heat generated at the center of the heater 415 when the humidity sensitive layer 430 is heated by the heater 415 to uniformly heat the humidity sensitive layer 430.

The sensing electrodes 414 is configured to sense a change in electrical characteristic of the humidity sensitive layer 430 according to the change in humidity around the sensor device. The sensing electrodes 414 includes a central sensing electrode 414b extending from the heater 415, and left and right sensing electrodes 414a and 414c, which are side sensing electrodes, extend from the electrode pad $E_S$. The sensing electrodes 414a, 414b and 414c are formed on the same plane as the electrode pads $E_H$, $E_S$, $E_G$, $E_{T1}$ and $E_{T2}$.

The central sensing electrode 414b is the microelectrode fingers extending from the heater 415, which may be formed in a comb or fishbone shape.

The side sensing electrodes 414a and 414c include the left and right sensing electrodes 414a and 414c extending from ends of the electrode pad $E_S$, respectively. The left and right sensing electrodes 414a and 414c are electrically connected with the electrode pad $E_S$.

The central sensing electrode 414b includes at least one branched microelectrode finger attached at both sides of the heater 415 having a bridge structure in a cantilever array, and forms a pair of interdigitated electrodes (IDEs) separated from each other with each of the side sensing electrodes 414a and 414c.

That is, each of the sensing electrodes 414a, 414b and 414c includes at least one microelectrode finger formed in a cantilever array. One end of each sensing electrode is disposed in the middle of the device and forms a pair of IDEs with another sensing electrode. The other end is connected to the corresponding electrode pad $E_H$, $E_S$, and $E_G$ for stable connection with an external electric wire.

A difference in electrical characteristic between the central sensing electrode 414b and the side sensing electrodes 414a and 414c, which form pairs of the IDEs, is output to an external circuit, and used to quantify humidity, which is an amount of moisture captured by the humidity sensitive layer 430.

In the sensing electrodes 414, a microelectrode finger spacing (microelectrode spacing) d may be the same as another microelectrode finger spacing, ranging from about 0.1 to 10 μm.

Figure 5A:
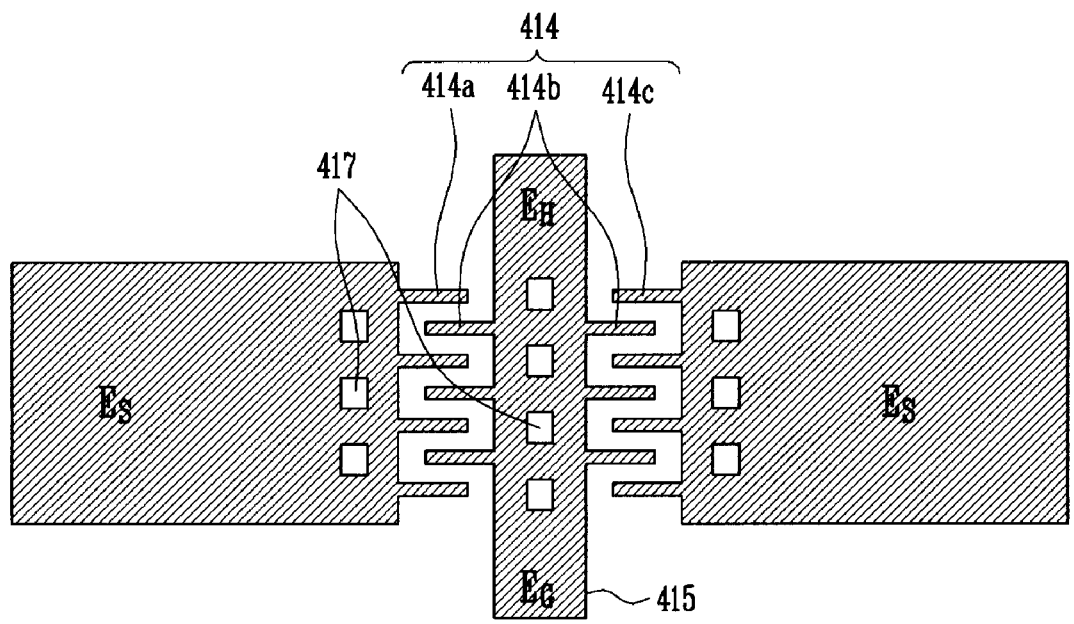
FIGS. 5A and 5B are enlarged views of a part of the humidity sensor according to an exemplary embodiment of the present invention.
Figure 5B:
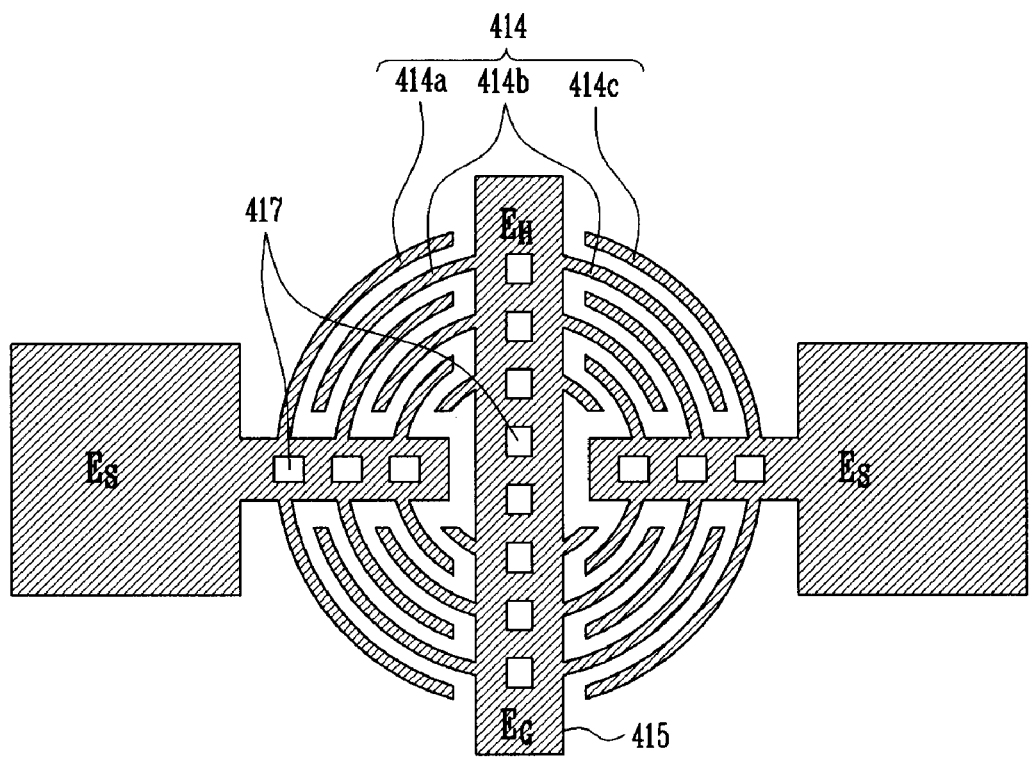

FIGS. 5A and 5B are enlarged plan views of a part of the humidity sensor according to exemplary embodiments of the present invention, in which electrode pads $E_H$, $E_S$ and $E_G$, sensing electrodes 414, a heater 415 and etch slots 417 are included.

FIG. 5A shows a linear-type sensing electrode 414, and FIG. 5B shows a circular-type sensing electrode 414. Here, three sensing electrodes 414a, 414b and 414c form pairs of IDEs to sense humidity. Among them, the central sensing electrode 414b, as described above, is combined with the heater 415 to uniformly heat the humidity sensing layer 430. The shapes of the sensing electrodes 414 and the heater 415 are not limited to those described with reference to FIG. 5. The etch slots 417 is provided to facilitate the flow of gas during etching of the substrate 401, which will be described in detail below.

Referring again to FIGS. 4A and 4B, the humidity sensitive layer 430 according to the exemplary embodiment of the present invention captures moisture used to measure ambient humidity, and may be formed of any one of the materials whose electrical characteristics are dependent on the ambient humidity. The materials may include an organic material, an inorganic material, a nano material, or a combination thereof.

The humidity sensitive layer 430 may be formed by one of micro dropping, e-beam evaporation, sputtering, pulsed laser deposition, sol-gel coating, chemical vapor deposition (CVD), spray coating, dip coating and screen printing.

When the humidity sensitive layer 430 is formed by micro dropping using a drop of a liquid precursor, even if the liquid precursor is dropped without exactly aligning a die, the liquid precursor dropped on the electrode pads $E_H$, $E_S$, and $E_G$ beyond the sensing electrodes is dried along the edge of an electrode pad separation groove 418 due to surface tension, without contacting the bottom substrate. Accordingly, the edges of the electrode pads are boundaries where the humidity sensitive layer 430 is formed. Thus, the humidity sensitive layer 430 is electrically connected on the sensing electrodes 414 patterned in a fine microstructure, not on the wide electrode pads $E_H$, $E_S$ and $E_G$.

To this end, a width c of the electrode pad separation groove 418 is generally greater than the spacings d between the central sensing electrode 414b, the left sensing electrode 414a and the right sensing electrode 414c, which include microelectrode fingers. Here, the width c ranges from about 10 to 100 μm.

As described above, when the humidity sensitive layer 430 is formed by micro dropping in the process of manufacturing the humidity sensor according to the present invention, it can prevent additional expenses for an expensive mechanical alignment system.

A die separation part 450 according to the exemplary embodiment of the present invention is formed on the substrate 401 to have a predetermined depth and width to facilitate separation of devices.

The etch slots 417 according to the exemplary embodiment of the present invention is formed to facilitate the formation of a suspended structure during the formation of the open cavity 416.

Meanwhile, to more precisely measure humidity, it is necessary to quantify a change in temperature around the sensor. Therefore, the humidity sensor according to the exemplary embodiment of the present invention includes an ambient temperature measurement part 420, which includes a resistance temperature detector (RTD) 425 having different resistances according to the temperature and electrode pads $E_{T1}$ and $E_{T2}$ for temperature measurement transferring the measured resistance to outside.

The RTD 425 has a stacked structure of the insulating layer 411 and the conductive layer 412, and is formed on the same plane as the electrode pads $E_H$, $E_S$, $E_G$, $E_{T1}$ and $E_{T2}$. The RTD 425 may be formed in a meander shape, and a spacing f of the RTD separation groove 428 also formed in a meander shape is designed to control a width thereof according to a desired resistance value, which may range from several tens to thousands of ohms.

The RTD separation groove 428 formed between the meander-shaped lines electrically insulates the meander-shaped lines from each other, and the RTD 425 from the substrate 401 to allow the RTD 425 to have an appropriate resistance value, and also insulates the substrate 401 from the RTD 425.

The electrode pads $E_{T1}$ and $E_{T2}$ for temperature measurement have a stacked structure of the insulating layer 411 and the conductive layer 412, and are formed on the same plane as the electrode pads $E_H$, $E_S$ and $E_G$ to transfer a resistance change of the RTD 425 to an external circuit.

The ambient temperature measurement part 420 is physically connected to the substrate 401. Here, the substrate 401 is in a thermal equilibrium with the surroundings, so that the temperature change of an atmosphere around the sensor may be quantified by measuring the property change of the RTD 425.

The resistance change is converted into temperature, which may be used as a reference temperature when the humidity sensitive layer 430 is heated by the heater 415, and as a reference temperature to precisely control the temperature of the heater 415 by closed loop control, and also used to appropriately control the temperature of the heater 415 by measurement steps of the sensor.

Meanwhile, when the suspended sensor structure is repeatedly heated by the heater and then cooled, thermal stress may be generated due to non-uniformity of temperature, resulting in damage to the structure.

However, the support layer 413 formed in combination of the insulating layer 411 and the conductive layer 412 according to the exemplary embodiment of the present invention has better thermal conductivity and durability than a single layer structure of a silicon oxide ($SiO_2$) layer or a silicon nitride ($Si_3N_4$) layer, which has bad thermal conductivity, or a stacked structure thereof. That is, since the non-uniformity of the temperature in this structure is decreased, thermal stress is reduced and the mechanical restoration force is increased, the sensor may be more resistant to thermal shock.

A method of manufacturing a humidity sensor according to an exemplary embodiment of the present invention will be described with reference to the accompanying drawings below.

FIGS. 6A to 6G are views illustrating a method of manufacturing a humidity sensor according to an exemplary embodiment of the present invention. Particularly, a method of manufacturing an entire sensor structure using one sheet of pattern mask will be described.

Figure 6A:
FIGS. 6A to 6G are diagrams illustrating a method of manufacturing a humidity sensor according to an exemplary embodiment of the present invention.

First, an insulating layer 411 is formed on a substrate 401 as shown in FIG. 6A.

The insulating layer 411 is used as an etching mask layer to form patterns for an open cavity 416, a heater 415, electrode pads $E_H$, $E_S$ and $E_G$, sensing electrodes 414, an RTD 425 and electrode pads $E_{T1}$ and $E_{T2}$ for temperature measurement in a subsequent process.

The insulating layer 411 also serves to electrically insulate the heater 415, the sensing electrodes 414, the electrode pads $E_H$, $E_S$ and $E_G$, the RTD 425 and the electrode pads $E_{T1}$ and $E_{T2}$ for temperature measurement from other portions such as the substrate 401 to minimize the affect of currents flowing through the above-mentioned structures on other portions such as the substrate 401, and becomes a part of a support layer 413 forming a bridge and cantilevers of a microstructure suspended from the substrate 401.

The insulating layer 411 may be formed of a silicon oxide ($SiO_2$) layer, a silicon nitride ($Si_3N_2$) layer, a modified $SiO_2$ layer selected from the group consisting of a borophosphosilicate glass (BPSG) layer, a phosphosilicate glass (PSG) layer and a spin-on-glass (SOG) layer, or a low-stress silicon nitride ($Si_XN_Y$) layer using low pressure chemical vapor deposition (LPCVD), plasma enhanced chemical vapor deposition (PECVD) or thermal oxidation.

The insulating layer 411 may be formed to a thickness of about 0.2 to 5 μm using a single- or multi-layered insulating material or a combination thereof.

Figure 6B:
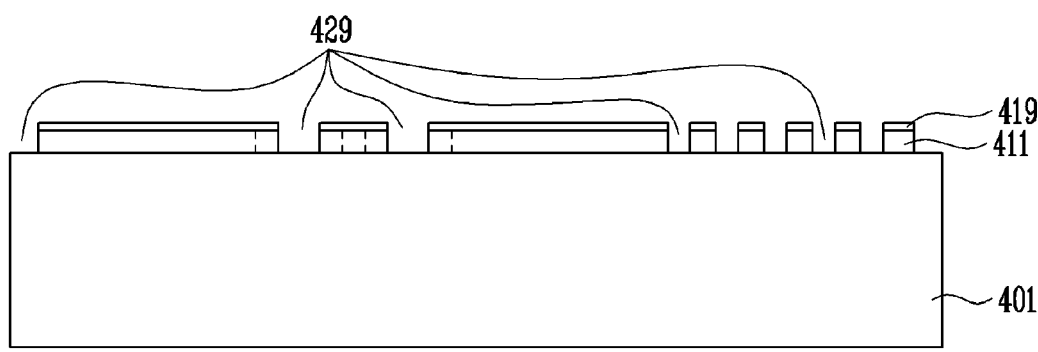

Afterward, as shown in FIG. 6B, a photoresist (PR) 419 is applied to the insulating layer 411 by spin coating, exposed using a pattern mask and then baked, developed and cleaned, thereby patterning the photoresist 419.

The pattern mask includes patterns for the open cavity 416, the heater 415, the electrode pads $E_H$, $E_S$ and $E_G$, the sensing electrodes 414, the RTD 425 and the electrode pads $E_{T1}$ and $E_{T2}$ for temperature measurement, the die separation part 450, the electrode pad separation groove 418, the RTD separation groove 428 and the etch slots 417, which will be formed in a subsequent process.

That is, according to the present invention, all the patterns of the components to be formed in a subsequent process may be formed at once using only one sheet of pattern mask. Thus, the production costs may be reduced, and the process may be simplified.

The patterned photoresist 419 is used as an etching mask layer to etch the insulating layer 411 and then washed, thereby forming a micro line width part 429 in the insulating layer 411.

Here, the insulating layer 411 may be patterned by dry etching such as reactive ion etching (RIE) using plasma or charged ion particles or wet etching using an etch solution as an etchant.

Figure 6C:
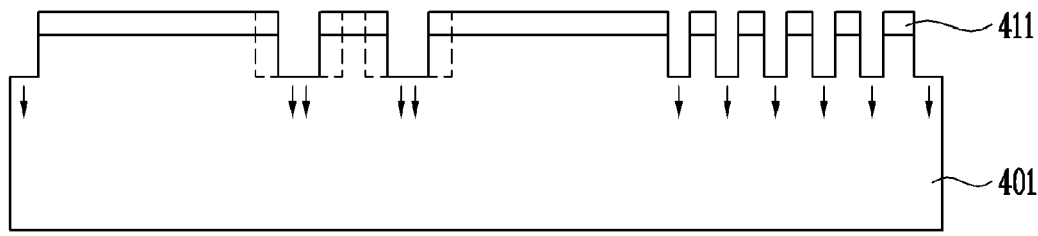

Then, as shown in FIG. 6C, a trench is formed in the substrate 401 using the insulating layer 411 as an etching mask layer. The trench may be formed by anisotropically etching the substrate along the arrow of FIG. 6C by RIE or deep-RIE capable of deeply etching the substrate in a vertical direction.

Meanwhile, approximate depths of the open cavity 416, the electrode pad separation groove 418, the RTD separation groove 428 and the die separation part 450 which will be formed in the subsequent process may be determined by the depth of the trench, which ranges from about 1 to 500 μm.

Figure 6D:
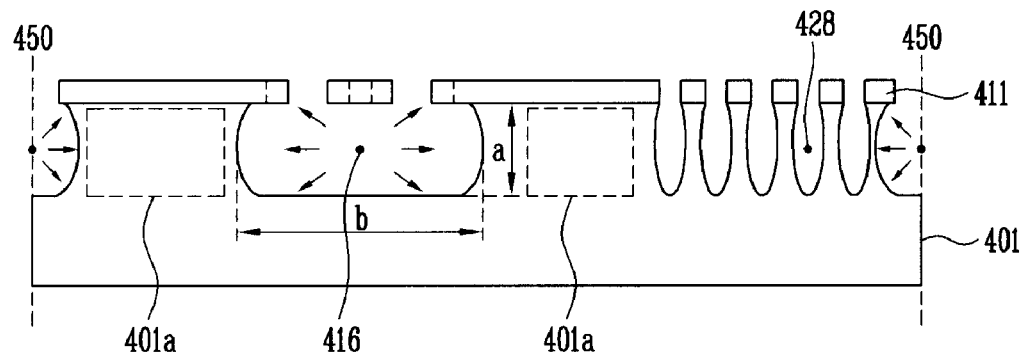

After that, as shown in FIG. 6D, the substrate 401 is isotropically etched using the insulating layer 411 as an etch masking layer along an arrow of FIG. 6D, thereby finally forming the open cavity 416, the electrode pad separation groove 418, the RTD separation groove 428, the die separation part 450 and the etch slots 417. Here, a portion that is not etched by the depth of the open cavity 416 becomes the anchor 401a to support the structures formed on the substrate 401.

The open cavity 416 may be formed to have a depth of about 1 to 500 μm, and a width b of about 1 μm to 10 mm.

As described above, the suspended structure is formed by anisotropically and isotropically dry etching the substrate to entirely prevent stiction between the suspended structure and the substrate generated during removal of a sacrificial layer of a MEMS device due to the wet etching. Thus, damage to the humidity sensor during the manufacture process may be prevented and yield may be increased.

Meanwhile, in most conventional processes of manufacturing a MEMS device, pieces of a MEMS die manufactured in an intermediate step are separated from a wafer using a sawing machine, and a sacrificial layer is removed from each die piece. Thus, it is difficult to commercialize due to low yield and difficulty in handling, e.g., gripping.

However, according to one exemplary embodiment of the present invention, the die separation part 450 is formed at once in the step described with reference to FIG. 6D, so that the die of the humidity sensor can be treated at the entire wafer level without being separated in the intermediate step. Thus, this method has a great advantage in commercialization, yield and cost.

Meanwhile, a plurality of etch slots 417 may be previously formed in a random shape in the pattern for the heater 415 and the pattern for the electrode pad $E_S$ adjacent to the pattern for the sensing electrodes 414 to facilitate diffusion of an etching gas during the anisotropic and isotropic etching of the substrate (referring to FIGS. 4A, 5A and 5B), and thus to rapidly etch the substrate 401. Thus, the suspended structure may be easily formed.

Figure 6E:
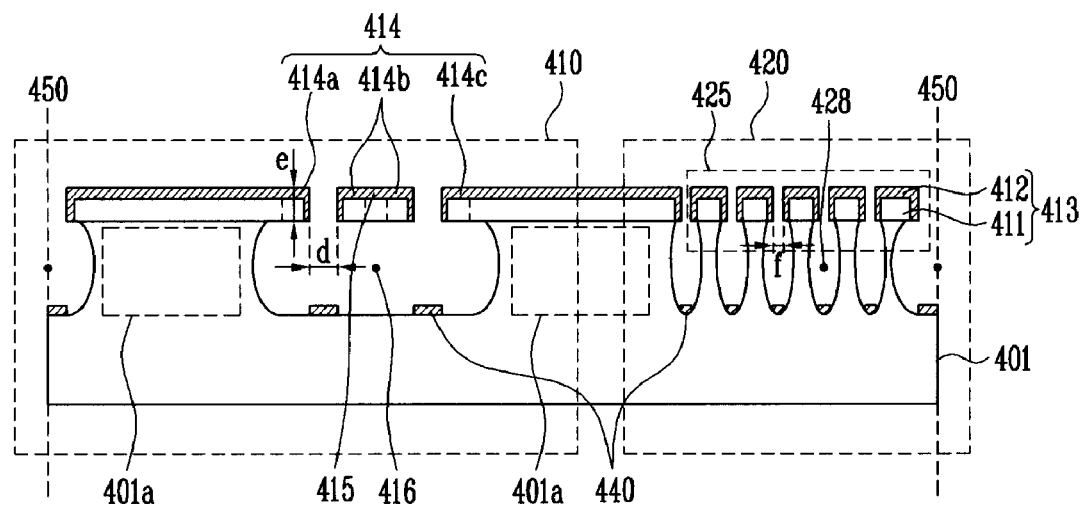

As shown in FIG. 6E, the heater 415, the sensing electrodes 414, the electrode pads $E_H$, $E_S$ and $E_G$, the RTD 425 and the electrode pads $E_{T1}$ and $E_{T2}$ for temperature measurement are simultaneously formed on the same plane by depositing the conductive layer 412 on the insulating layer 411.

The conductive layer 412 may be easily formed by a semiconductor process and exhibit stable operation characteristics. The conductive layer 412 is formed of a metal having excellent thermal resistance and physical chemical characteristics or a material including the metal.

Alternatively, a thin film may be deposited to a small thickness as a lower base layer by sputtering or e-beam evaporation to promote adherence to the insulating layer 411 and crystallization orientation and prevent diffusion of the component of the conductive layer 412 into the surrounding, and then another thin film may be deposited to an appropriate thickness on the lower base layer, thereby forming a double layer or a combination layer thereof.

Automatically, all the structures constituting the humidity sensor are electrically insulated and isolated from each other only by depositing the conductive layer 412 as described above.

While conductive layers 440 may be partially formed at lower portions of the open cavity 416, the electrode pad separation groove 418, the RTD separation groove 428 and the die separation parts 450 during the formation of the conductive layer 412, the conductive layers 440 are electrically insulated from the structures on the substrate 401 suspended by the anchor 401a, due to the presence of the insulating layer 411. Thus, an additional process of patterning a metal layer such as a general lift-off process is unnecessary.

The support layer 413 composed of the insulating layer 411 and the conductive layer 412 may be formed to a thickness e of about 0.3 to 10 μm.

Meanwhile, the heater 415 formed during the process should be designed to have low power consumption, fast response time and stable operation characteristics, and may be designed to have a resistance of several to several hundreds of ohms at room temperature.

As described above, according to the present invention, a humidity sensor structure composed of suspended microstructures having a random shape and various size and depth can be easily manufactured by a semiconductor process using only one pattern mask, unlike the conventional method requiring at least 3 to 10 pattern masks, to manufacture functional elements including a thermal insulation structure.

Figure 6F:
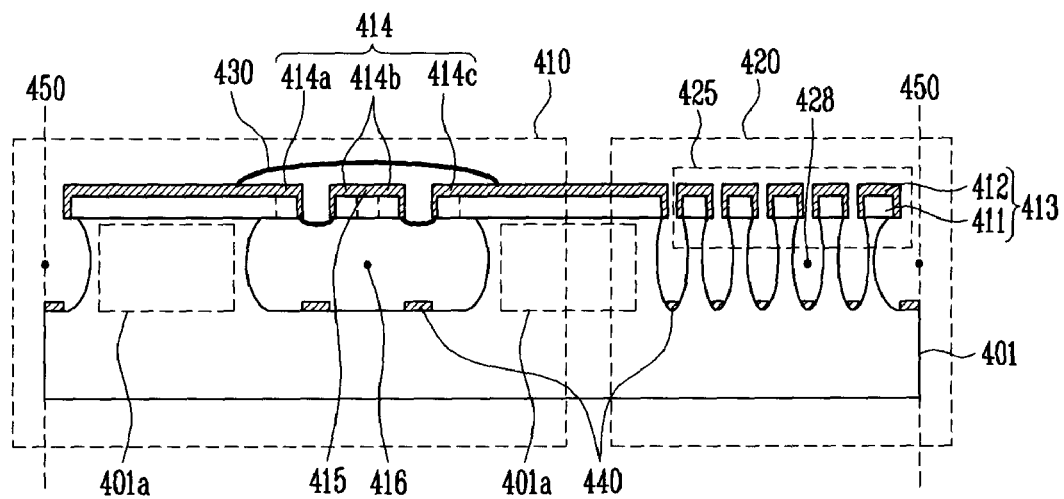

Then, as shown in FIG. 6F, a humidity sensitive layer 430 is formed on the structure suspended on the open cavity 416.

The humidity sensitive layer 430 may be formed by micro dropping, e-beam evaporation, sputtering, pulsed laser deposition, sol-gel coating, chemical vapor deposition (CVD), spray coating, dip coating or screen printing. Hereinafter, a method of forming the humidity sensitive layer 430 by micro dropping will be described.

To begin with, a liquid precursor for a humidity sensitive layer is prepared by mixing an organic material such as a polymer, an inorganic material such as ceramic or a nano material such as nano wires with a solvent or a mixture of a solvent and a binder in an appropriate ratio.

Subsequently, the liquid precursor is dropped once or several times in a volume of several to several tens of nano liters on a portion in which a pair of IDEs suspended on the open cavity 416 will be formed.

In the middle of the humidity sensor on which the liquid precursor is dropped, the pair of the IDEs are formed by three sensing electrodes 414 including four microelectrode fingers formed in a cantilever array, and an IDE finger spacing d ranges from about 0.1 to 10 μm. Here, the support layer 413 constituting the electrodes has a thickness of about 0.3 to 10 μm.

The liquid precursor dropped on the microstructure penetrates into a narrow gap between the microelectrodes in a depth direction of the support layer 413 due to capillary force, and hangs under the insulating layer 411 due to surface tension. However, the liquid precursor is not in contact with the underlying substrate 401 due to the deeply-formed open cavity 416.

As a liquid ingredient of the liquid precursor is gradually dried at room temperature, an even surface is made and thus only a solid ingredient of the liquid precursor remains to fill the gap between the microelectrodes.

After that, when the liquid precursor is additionally dried and heated, a remaining solvent or binder may be volatilized and thus only the humidity sensitive layer 430 is formed to a diameter of several tens of micrometers to several millimeters on the uppermost surface of the sensor device in a solid state.

Here, the liquid precursor dropped on the portions other than the structure suspended by the electrode pad separation groove 418 formed in an X shape (in FIG. 4A) is dried without contacting the substrate 401, and formed along the edges of the electrode pads $E_H$, $E_S$ and $E_G$ due to the surface tension.

Finally, only the humidity sensitive layer 430 formed on the suspended microstructure is electrically connected to the microelectrode fingers of the central sensing electrode 414b, and the left and right sensing electrodes 414a and 414c. As a result, in formation of the humidity sensitive layer 430 by micro dropping, micro patterning or precise alignment is unnecessary.

Accordingly, the humidity sensitive layer 430 capable of being formed of various materials may be directly formed only on the sensing electrodes 414 using the capillary force and the surface tension of a liquid without an additional process such as micro patterning.

When the humidity sensitive layer 430 is formed of a nano material such as a nano wire, sensing characteristics may be further improved by structurally aligning the corresponding material to connect both ends of the sensing electrodes 414. When the corresponding material is provided by micro dropping while a direct or alternating bias voltage is applied to the both ends of the pair of IDEs composed of the central sensing electrode 414b and the left and right sensing electrodes 414a and 414c, the nano wire may be aligned in a fine structure on the both ends of the IDEs to be connected to each other due to the potential difference between the IDEs. Thus, the humidity sensitive layer may be more effectively formed.

After the humidity sensor device is installed in a vacuum reaction furnace, when a source material for depositing a nano material is provided and a bias voltage is applied to both ends of the heater 415 of the sensor device, due to the thermal insulation structure formed by the open cavity 416 and the micro-suspended structure, the nano material is deposited on the central sensing electrode 414b heated to high temperature and then grown with time to be connected to the left and right sensing electrodes 414a and 414c. As a result, the humidity sensitive layer 430 formed of a nano material may be formed only on the sensing electrodes 414 in situ without micro patterning.

The kind of the material for the humidity sensitive layer 430 is not limited, and thus any kind of material that is changed in electrical characteristic according to the change in humidity of the surroundings can be used. Finally, the humidity sensitive layer 430 formed to a desired thickness is thermally treated at an appropriate temperature and in an appropriate atmosphere to obtain improvement in quality and stability of the thin film used as the sensitive layer.

For subsequent packaging and assembly processes such as die attachment using an adhesive or soldering and wire bonding, the substrate 401 of the humidity sensor device having the humidity sensor layer 430 is divided and separated by dies at a wafer level.

That is, the humidity sensor device dies on the substrate wafer are separated at once using the die separation part 450 previously formed to divide the wafer by dies, and then packaged.

Figure 6G:
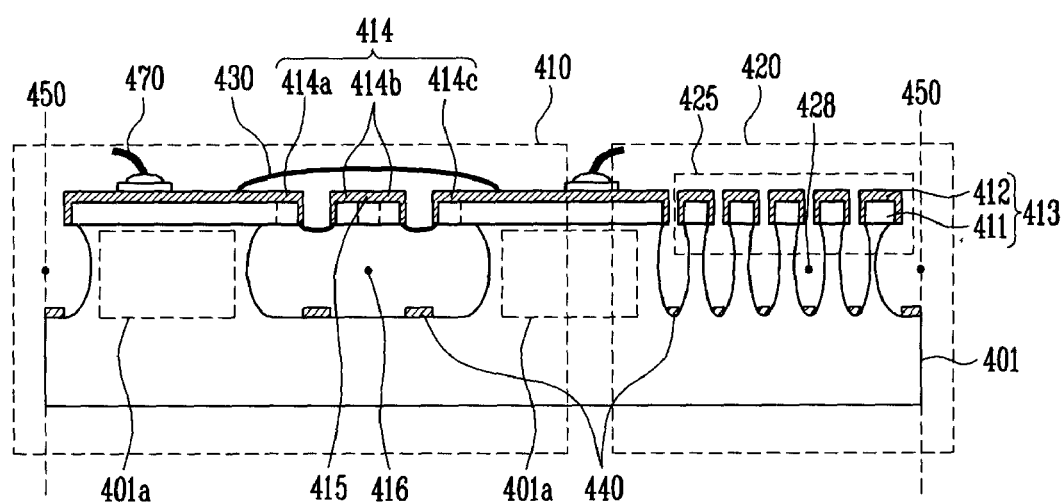

FIG. 6G is a schematic view of the humidity sensor device on which the wire bonding 470 is completed. Accordingly, a metal conductive wire is bonded on five electrode pads $E_H$, $E_S$, $E_G$, $E_{T1}$ and $E_{T2}$ formed to connect the heater 415, the central sensing electrode 414b, the left sensing electrode 414a, the right sensing electrode 414c and the RTD 425 to an external electric conductive wire in the separated die of the humidity sensor device. Detailed steps during the packaging and assembly process are common in manufacture of the sensor device, so that the detailed descriptions thereof will be omitted for convenience.

Figure 1:
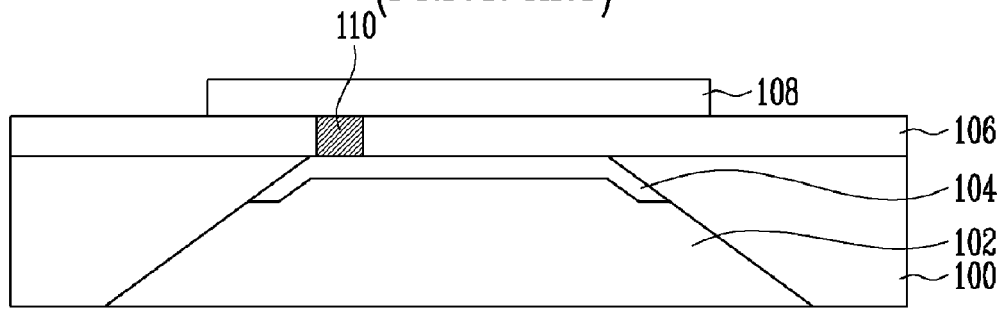
Figure 2:
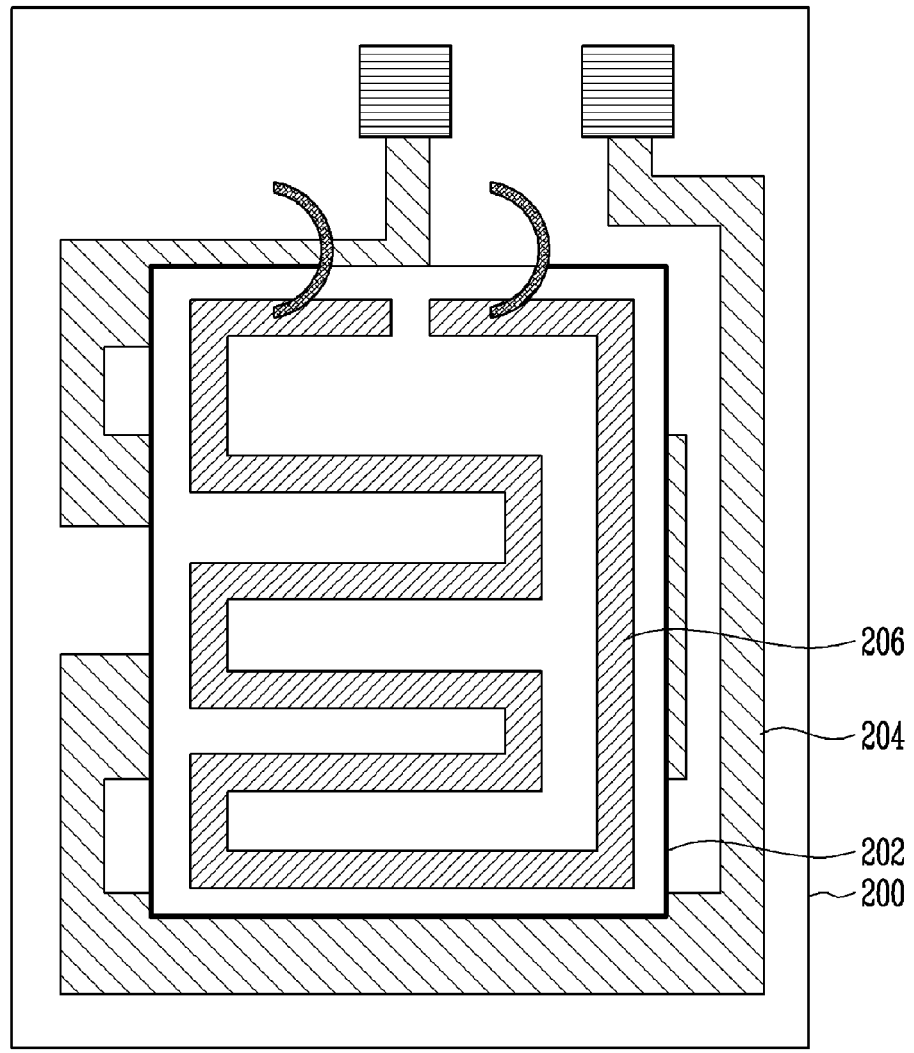

Meanwhile, in the conventional humidity sensor device formed by wet silicon etching (referring to FIG. 1), a suspended structure has an insulating layer deposited on a front surface of the substrate, which is formed in a specific shape by etching the silicon substrate in an anisotropic crystallization direction by a thickness thereof through an opening of a square-shaped pattern formed on a back surface of the silicon substrate in a frequently-used <100> crystallization direction using a wet silicon etching solution such as potassium hydroxide (KOH), tetramethylammonium hydroxide (TMAH) or ethylenediamine pyrocatechol (EDP). Here, during the formation of the suspended structure, a main etch front formed in a <111> crystallization direction and thus an open cavity formed at an angle of 54.7° are simultaneously manufactured. While the overall shape of the suspended structure is generally square, if not, another pattern should be used for etch compensation at edges of the suspended structure.

However, in the method of manufacturing the humidity sensor according to the exemplary embodiment of the present invention, dry etching is performed only on the front side of the substrate to form the suspended structure of the humidity sensor device. Thus, the suspended structure can be manufactured in a random shape regardless of the width and thickness of the substrate according to the crystallization direction of the substrate. Consequently, according to the present invention, if the cavities are formed in the same size, as the die of the device is decreased in size, the total number of the dies obtained within a given diameter of the wafer is increased. Thus, the decrease in package size and the decrease in defect density and drift in the process can lead to the improvement in quality. Moreover, as the size of the final package is decreased, the production costs of the device can be greatly reduced. That is, the humidity sensor described in the present invention can be massively manufactured in a high-precision and ultra small-sized suspended structure at a low cost using dry etching performed on the front surface of the substrate, compared to the conventional wet etching performed on the back surface of the substrate.

Figure 7A:
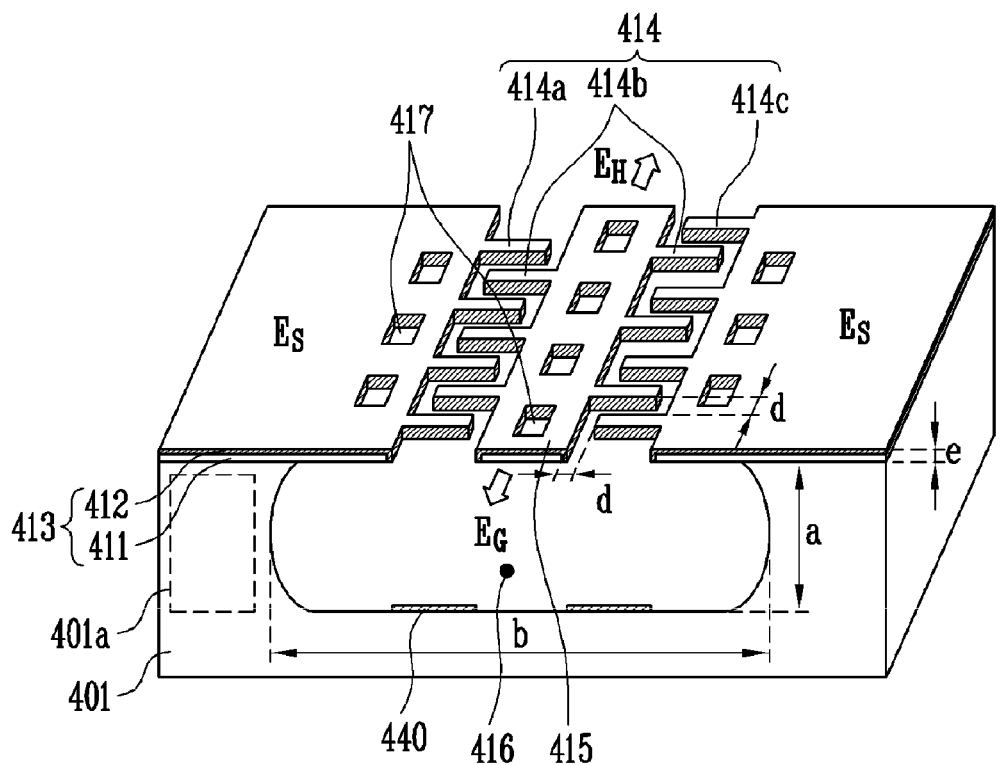
FIGS. 7A and 7B are diagrams illustrating an operation of a humidity sensor according to an exemplary embodiment of the present invention.
Figure 7B:
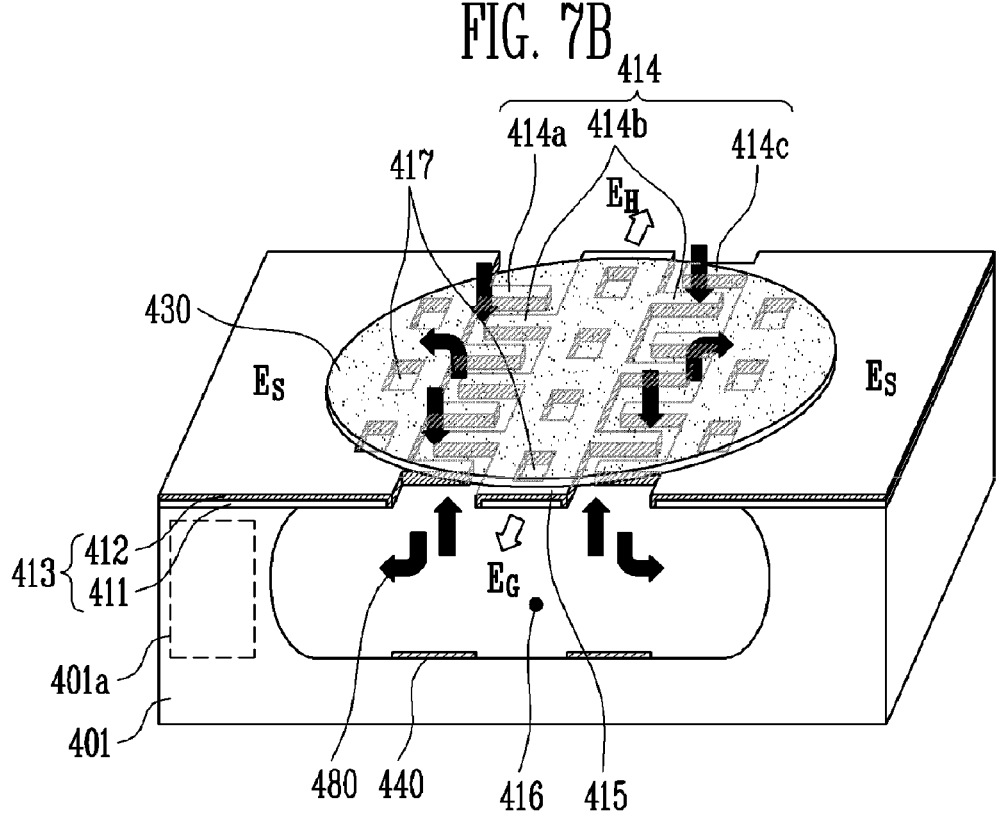

FIGS. 7A and 7B are a schematic diagram of an enlarged portion including sensing electrodes and a humidity sensitive layer formed thereon in a humidity sensor to illustrate a sensing principle of the humidity sensor according to the exemplary embodiment of the present invention.

Referring to FIG. 7A, a open cavity 416 may be formed to a depth a of about 1 to 500 μm and a width b of about 1 μm to 10 mm in a substrate 401, and a support layer 413, which is composed of an insulating layer 411 and a conductive layer 412, is formed to a thickness e of about 0.3 to 10 μm in a microstructure, and suspended in the air over the substrate 401.

In the suspended microstructure, the sensing electrodes 414 is composed of three sensing electrodes 414a, 414b and 414c, which include microelectrode fingers formed in a cantilever array, thereby forming a pair of IDEs facing each other. Spacings d between IDE microelectrodes are the same as one another, usually ranging from about 0.1 to 10 μm. A heater 415 formed in a bridge shape is disposed in the middle of the sensing electrodes 414, and the central sensing electrode 414b including several microelectrode fingers extends from the heater 415 to uniformly distribute heat emitted from the heater 415. These structures may be more easily suspended by forming a plurality of etch slots 417 in the bridge of the heater 415, and the electrode pad $E_S$ connected to the left sensing electrode 414a and the right sensing electrode 414c and increasing the area of the substrate 401 in contact with a dry etching gas.

FIG. 7B shows a humidity sensor device including the humidity sensitive layer 430 formed by appropriately drying and thermally treating the liquid precursor dropped on the pair of IDEs and the bridge of the heater 415, which are suspended on the open cavity 416, by micro dropping.

The humidity sensitive layer 430 is formed in a solid state to fill gaps between the plurality of IDEs formed in a cantilever array (referring to FIG. 7A) due to the surface tension and capillary force, and is suspended over the open cavity 416 and in contact with the bridge of the heater 415. An entire outer diameter of the humidity sensitive layer 430 ranges from several tens of micrometers to several millimeters.

In the conventional humidity sensor having a common planar electrode structure, since a lower portion of the humidity sensitive layer is enclosed with a solid layer, gases may be transferred only through an upper portion of the humidity sensitive layer in direct contact with an external gas by adsorption and desorption. Moreover, due to the characteristic of a planar electrode, the electrode is in contact with the humidity sensitive layer in a small area, so that the humidity sensor generally has low sensitivity and delayed response time.

However, according to the present invention, the humidity sensitive layer 430 is formed to fill the gap d between the microelectrode fingers each having a depth of about 0.3 to 10 μm in a vertical direction, so that the entire surface area in direct contact with the pair of IDEs is much larger than that of the conventional planar electrode structure, and an output of the device, i.e., sensitivity of the humidity sensor, corresponding to the humidity change in the surroundings, is greatly enhanced. Moreover, since the humidity sensitive layer 430 is suspended in the air, the gas 480 containing moisture is diffused into a three-dimensional space including the open cavity 416, the etch slots 417 and the upper portion of the device (toward the arrow points in FIG. 7B) and rapidly adsorbed to and desorbed from the humidity sensitive layer 430, resulting in increases in response time and sensitivity of the humidity sensor.

To measure the humidity around the sensor, when a predetermined electrical power is applied to both ends of the electrode pads $E_H$ and $E_G$ connected to the bridge of the heater 415 and generally having a resistance of several to several hundreds of ohms, the humidity sensitive layer 430 formed by filling the gap between the micro sensing electrode fingers is uniformly heated to a predetermined temperature by the central sensing electrode 414b serving as a heat spreader. The gas 480 containing moisture present in the surroundings is adsorbed to or desorbed from the humidity sensitive layer 430, thereby leading to a fine change in property of the humidity sensitive layer 430. This characteristic change is measured with the humidity sensor connected to an external electric circuit, for instance by measuring a potential difference between the electrode pad $E_S$ and the ground electrode pad $E_G$, by quantifying the change in electrical characteristic of the humidity sensitive layer 430, and by converting the quantified result into the humidity around the humidity sensor.

Here, the temperature around the humidity sensor measured using the RTD 425 (referring to FIG. 4A) generally having a resistance of several tens to thousands of ohms is used as a reference temperature for closed loop control to heat the heater 415 to a specific temperature or precisely maintain the temperature of the heater 415 depending on the humidity measurement steps.

And, after the humidity sensitive layer 430 is reset to an initial state by heating other gases previously adsorbed on the humidity sensitive layer 430 or the gas 480 containing moisture at a high temperature using the heater 415 to forcibly remove the other gases, the humidity of the gas of interest may be measured.

Properly heating the heater by measurement steps may prevent deterioration caused by excessive condensation of moisture in the humidity sensitive layer and minimize the change in measured signal and hysteresis. In addition, since the sensor can be easily reset to the initial state, the response time can be shortened and sensitivity can be increased.

According to the present invention, a humidity sensor can have high sensitivity to humidity, quick response time, low hysteresis, improved temperature characteristics, low power consumption, and excellent durability. In addition, the humidity sensor can have a humidity sensitive layer easily formed of various materials. Moreover, an ultra small-sized humidity sensor can be produced in a large scale with high yield using only one sheet of pattern mask.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A humidity sensor, comprising:
a substrate;
an open cavity with an open upper portion, the open cavity being formed to have a depth and a width in the substrate;
a plurality of electrode pads formed on the substrate;
a heater connected to one pad of the electrode pads at a first end and connected to another pad of the electrode pads at a second end and suspended over the open cavity;
a plurality of sensing electrodes formed on the same plane as the heater, and suspended over the open cavity to output a sensed signal to the electrode pads;
a humidity sensitive layer formed on the heater and the sensing electrodes suspended over the open cavity, and changed in characteristic according to the humidity; and
an ambient temperature measurement part configured to measure the temperature around the humidity sensor, wherein the temperature is used as a reference temperature to control a heating temperature of the heater,
wherein the heater is formed in a bridge shape and disposed in the middle of the upper portion of the open cavity, the heater including comb-shaped branches at both sides.

2. The humidity sensor according to claim 1, wherein the substrate is formed of one of a semiconductor, a conductor and an insulator.

3. The humidity sensor according to claim 1, wherein the sensing electrodes includes a central sensing electrode connected to the heater at one end and suspended over the open cavity, and side sensing electrodes electrically insulated from the heater and suspended over the open cavity, the side sensing electrodes including left and right sensing electrodes disposed at both sides of the central sensing electrode, respectively.

4. The humidity sensor according to claim 3, wherein the central sensing electrode is connected to the heater and includes a plurality of microelectrode fingers formed in a comb or fishbone array.

5. The humidity sensor according to claim 3, wherein each of the side sensing electrodes includes a plurality of microelectrode fingers formed in a cantilever array.

6. The humidity sensor according to claim 3, wherein the central sensing electrode and the side sensing electrodes face each other to form a pair of interdigitated electrodes (IDEs).

7. The humidity sensor according to claim 1, wherein the humidity sensitive layer covers the heater and fills gaps between microelectrode fingers comprising the sensing electrodes due to capillary force and surface tension.

8. The humidity sensor according to claim 1, wherein the humidity sensitive layer is formed of at least one of an organic, inorganic and nano material.

9. The humidity sensor according to claim 1, further comprising an electrode pad separation groove formed in the substrate to electrically insulate the plurality of electrode pads from each other, and allowing the humidity sensitive layer to be formed along edges of the plurality of electrode pads, not in contact with the underlying substrate.

10. The humidity sensor according to claim 1, wherein the ambient temperature measurement part includes a resistance temperature detector (RTD) changed in resistance according to the temperature, and a plurality of electrode pads for temperature measurement connected to both ends of the RTD.

11. The humidity sensor according to claim 10, wherein the ambient temperature measurement part further includes an RTD separation groove electrically insulating the RTD from the underlying substrate, and in physical contact with the substrate.

12. The humidity sensor according to claim 1, wherein the electrode pad, the heater, the sensing electrodes, the RTD and the electrode pad for temperature measurement are all formed on the same plane, and formed by stacking at least one insulating layer and one conductive layer.

13. The humidity sensor according to claim 1, further comprising a die separation part formed in the substrate to separate the sensor by dies.

14. The humidity sensor according to claim 1, further comprising a plurality of etch slots formed in the heater and the electrode pads to help the formation of a suspended microstructure.

15. A method of manufacturing a humidity sensor, comprising:
forming an insulating layer on a substrate;
forming an electrode pad pattern, a heater pattern, a sensing electrode pattern, a resistance temperature detector (RTD) pattern and an electrode pad pattern for temperature measurement by patterning the insulating layer using a pattern mask;
forming etch slots in the electrode pad pattern and the heater pattern to facilitate diffusion of the gas during the etching of the substrate;
forming an open cavity in the substrate to suspend the heater pattern and the sensing electrode pattern;
forming electrode pads, a heater, sensing electrodes, an RTD and electrode pads for temperature measurement by depositing a conductive layer on the electrode pad pattern, the heater pattern, the sensing electrode pattern, the RTD pattern and the electrode pad pattern for temperature measurement; and
forming a humidity sensitive layer to cover the heater and the sensing electrodes.

16. The method according to claim 15, wherein forming the open cavity includes forming a trench structure by anisotropically etching the substrate in a vertical direction using the insulating layer pattern as an etching mask layer; and
forming the open cavity by isotropically etching the trench structure again.

17. The method according to claim 15, wherein the humidity sensitive layer is formed to fill gaps between the sensing electrodes or formed along edges of the sensing electrodes using surface tension and capillary force of a liquid precursor.

18. The method according to claim 15, further comprising forming a die separation part to facilitate separation of the humidity sensor.

* * * * *